US008283466B2

(12) United States Patent
Frost

(10) Patent No.: US 8,283,466 B2
(45) Date of Patent: Oct. 9, 2012

(54) CATALYTIC DEAMINATION FOR CAPROLACTAM PRODUCTION

(75) Inventor: John W. Frost, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 239 days.

(21) Appl. No.: 12/527,848

(22) PCT Filed: Feb. 20, 2008

(86) PCT No.: PCT/US2008/002202
§ 371 (c)(1),
(2), (4) Date: Jan. 22, 2010

(87) PCT Pub. No.: WO2008/103366
PCT Pub. Date: Aug. 28, 2008

(65) Prior Publication Data
US 2010/0145003 A1    Jun. 10, 2010

Related U.S. Application Data

(60) Provisional application No. 60/902,211, filed on Feb. 20, 2007.

(51) Int. Cl.
*C07D 201/02* (2006.01)
*C07D 201/08* (2006.01)
(52) U.S. Cl. .................................. 540/538; 546/245
(58) Field of Classification Search .............. 540/538; 546/245
See application file for complete search history.

(56) References Cited

U.S. PATENT DOCUMENTS

| 2,142,007 A | 12/1938 | Schlack |
| 2,241,321 A | 5/1941 | Schlack |
| 2,979,439 A | 4/1961 | Kinoshita et al. |
| 3,018,273 A | 1/1962 | Butler et al. |
| 3,625,923 A | 12/1971 | Roberts |
| 3,687,810 A | 8/1972 | Kurihara et al. |
| 3,707,441 A | 12/1972 | Shiio et al. |
| 3,862,262 A | 1/1975 | Hendrick et al. |
| 3,871,960 A | 3/1975 | Kubota et al. |
| 3,925,325 A | 12/1975 | Heimsch et al. |
| 3,965,375 A | 6/1976 | Bergman, Jr. et al. |
| 4,022,683 A | 5/1977 | Blundis et al. |
| 4,031,164 A | 6/1977 | Hedrick et al. |
| 4,034,015 A | 7/1977 | Hedrick et al. |
| RE30,371 E | 8/1980 | Hedrick et al. |
| 4,223,112 A | 9/1980 | Hedrick et al. |
| 4,275,157 A | 6/1981 | Tosaka et al. |
| 4,368,115 A | 1/1983 | Chianelli et al. |
| 4,411,997 A | 10/1983 | Shimazaki et al. |
| 4,465,790 A | 8/1984 | Quayle |
| 4,520,021 A | 5/1985 | Harris et al. |
| 4,601,829 A | 7/1986 | Kaneko et al. |
| 4,615,742 A | 10/1986 | Wright |
| 4,617,090 A | 10/1986 | Chum et al. |
| 4,623,623 A | 11/1986 | Nakanishi et al. |
| 4,692,520 A | 9/1987 | Van Geenen et al. |
| 4,706,903 A | 11/1987 | Brink et al. |
| 4,716,142 A | 12/1987 | Laine et al. |
| 4,739,064 A | 4/1988 | Shaw |
| 4,740,487 A | 4/1988 | Matheson et al. |
| 4,752,579 A | 6/1988 | Arena et al. |
| 4,787,939 A | 11/1988 | Barker et al. |
| 4,826,819 A | 5/1989 | Vecchietti et al. |
| 4,861,722 A | 8/1989 | Sano et al. |
| 4,908,312 A | 3/1990 | Ozaki et al. |
| 4,954,441 A | 9/1990 | Katsumata et al. |
| 4,959,452 A | 9/1990 | Meyer et al. |
| 4,963,486 A | 10/1990 | Hang |
| 5,032,664 A | 7/1991 | Frauendorf et al. |
| 5,047,332 A | 9/1991 | Chahal |
| 5,177,009 A | 1/1993 | Kampen |
| 5,221,357 A | 6/1993 | Brink |
| 5,236,831 A | 8/1993 | Katsumata et al. |
| 5,250,423 A | 10/1993 | Murakami et al. |
| 5,252,199 A | 10/1993 | Singhai et al. |
| 5,258,300 A | 11/1993 | Glassman et al. |
| 5,278,121 A | 1/1994 | Singhai et al. |
| 5,409,600 A | 4/1995 | Weissman et al. |
| 5,628,830 A | 5/1997 | Brink |
| 5,639,744 A | 6/1997 | Marchi et al. |
| 5,650,304 A | 7/1997 | Ishii et al. |
| 5,798,237 A | 8/1998 | Picataggio et al. |
| 5,807,870 A | 9/1998 | Anderson et al. |

(Continued)

FOREIGN PATENT DOCUMENTS

DE          748253          6/1938

(Continued)

OTHER PUBLICATIONS

Achkar, Jihane, et al., "Biosynthesis of Phloroglucinol," Journal of the American Chemical Society, vol. 127, pp. 5332-5333, (2005).
Anastassiadis, Savas, "L-Lysine Fermentation," Recent Patents on Biotechnology, vol. 1, pp. 11-24, (2007).
Angelucci, Luciano, et al., "Synthesis and amnesia-reversal activity of a series of 7- and 5-membered 3-acylamino lactams," Journal of Medicinal Chemistry, vol. 36, No. 11, pp. 1511-1519, (1993).
Beech J.S., et al., "Neuroprotection in ischemia-reperfusion injury: an antiinflammatory approach using a novel broad-spectrum chemokine inhibitor," Journal Cerebral Blood Flow & Metabolism, vol. 21, pp. 683-689, (2001).
Beech J.S., et al., "The MHP36 Line of Murine Neural Stem Cells Expresses Functional CXCR1 Chemokine Receptors that Initiate Chemotaxis In Vitro," Journal of Neuroimmunology, vol. 184, pp. 198-208, (2007).

(Continued)

*Primary Examiner* — Bruck Kifle
(74) *Attorney, Agent, or Firm* — Harness, Dickey & Pierce, P.L.C.

(57) ABSTRACT

Catalytic processes for preparing caprolactam, pipecolinic acid, and their derivatives, from lysine or alpha-amino-epsilon-caprolactam starting materials, and products produced thereby. A process for preparing caprolactam or a derivative thereof, the process comprising contacting a reactant comprising lysine or alpha aminocaprolactam with a catalyst and a gas comprising hydrogen gas, in the presence of a solvent. The catalyst may be provided on a support material, such as a transition metal.

46 Claims, No Drawings

U.S. PATENT DOCUMENTS

| | | | |
|---|---|---|---|
| 5,840,358 | A | 11/1998 | Höfler et al. |
| 5,855,767 | A | 1/1999 | Powers et al. |
| 5,868,851 | A | 2/1999 | Lightner |
| 6,022,419 | A | 2/2000 | Torget et al. |
| 6,096,885 | A | 8/2000 | Dezube et al. |
| 6,162,351 | A | 12/2000 | Sudhakar et al. |
| 6,228,177 | B1 | 5/2001 | Torget |
| 6,267,874 | B1 | 7/2001 | Iijima et al. |
| 6,379,934 | B1 | 4/2002 | Tilg et al. |
| 6,403,844 | B1 | 6/2002 | Zhang et al. |
| 6,504,047 | B2 | 1/2003 | Knaup |
| 6,610,530 | B2 | 8/2003 | Blank et al. |
| 6,620,292 | B2 | 9/2003 | Wingerson |
| 6,670,156 | B1 | 12/2003 | Möckel et al. |
| 6,692,578 | B2 | 2/2004 | Schmidt et al. |
| 7,112,312 | B2 | 9/2006 | Chou |
| 2001/0056184 | A1 | 12/2001 | Noda et al. |
| 2006/0258638 | A1 | 11/2006 | Olson et al. |

FOREIGN PATENT DOCUMENTS

| | | |
|---|---|---|
| GB | 1067153 | 5/1967 |
| JP | 2003-17062 | 1/1991 |
| JP | 2003/145933 | 5/2003 |
| JP | 2003/206276 | 7/2003 |
| WO | 2005/123669 | 12/2005 |
| WO | 2007/017610 | 2/2007 |
| WO | 2007/101867 | 9/2007 |

OTHER PUBLICATIONS

Belyaev, Alexander A., "A Novel Synthetic Route to Enantiomers of ε-Hydroxynorleucine and ε-Chloronorleucine from L- and D,L-Lysine," Tetrahedron Letters, vol. 36, No. 3, pp. 439-440, XP002348860, (1995).

Blade-Font, "Facile synthesis of γ-, δ-, and ε-lactams by cyclodehydration of ω-amino acids on alumina or silical gel," Tetrahedron Letters, vol. 21, pp. 2443-2446, (1980).

Chen, M.S., et al., "The Structure of Catalytically Active Gold on Titania," Science, vol. 306, pp. 252-255, (2004).

Corma, A., et al., "Chemoselective Hydrogenation of Nitro Compounds with Supported Gold Catalysts," Science, vol. 313, pp. 332-334, (2006).

Couty, F., "Asymmetric Syntheses of Pipecolic Acid and Derivatives," Amino Acids, vol. 16, No. 3-4, pp. 297-320, (1999).

Doldouras et al., "A direct, selective, and general method for reductive deamination of primary amines," J. Am. Chem. Soc. vol. 100, pp. 341-342, (1978).

Egorova et al., "On the role of β hydrogen atoms in the hydrodenitrogenation of 2-methylpyridine and 2-methylpiperidine," J. Catalysis, vol. 206, pp. 263-271, (2002).

Eijsbouts et al., "Periodic trends in the hydrodenitrogenation activity of carbon-supported transition metal sulfide catalysts," J. Catalysis, vol. 109, pp. 217-220, (1988).

Fox, David J., et al., "Design, Synthesis and Preliminary Pharmacological Evaluation of N-Acyl-3-aminoglutarimides as Broad-Spectrum Chemokine Inhibitors in Vitro and Anti-inflammatory Agents in Vivo," Journal of Medicinal Chemistry, vol. 45, pp. 360-370, (2002).

Fox, David J., et al., "Identification of 3-(Acylamino)azepan-2-ones as Stable Broad-Spectrum Chemokine Inhibitors Resistant to Metabolism in Vivo," Journal of Medicinal Chemistry, vol. 48, No. 3, pp. 867-874, (2005).

Frow, E.K., et al., "Tools for Anti-Inflammatory Drug Design: In Vitro Models of Leukocyte Migration," Meddicinal Research Reviews vol. 24, No. 3, pp. 267-298, (2004).

Goto et al., "Synthesis of 2-Amino-ε-caprolactam by Cyclodehydration of Lysine in Subcritical Water," J. Chem. Eng. of Japan, vol. 37, No. 2. pp. 353-356, (2004).

Grainger, D.J., et al., "Broad Spectrum Chemokine Inhibitors Related to NR58-3.14.3," Mini-Reviews in Medicinal Chemistry, vol. 5, pp. 825-832, (2005).

Grainger, D.J., et al., "Blockade of chemokine-induced signaling inhibits CCR5-dependent HIV infection in vitro without blocking gp 120/CCR5 interaction," Retrovirology, vol. 2, p. 1-9, (2005).

Grainger, D.J., et al., "Broad-spectrum chemokine inhibitors (BSCIs) and their anti-inflammatory effect in vivo," Biochemical Pharmacology., vol. 65, pp. 1027-1034, (2003).

Guttieri et al., "Selective cleavage of carbon-nitrogen bonds with platinum," Journal of Organic Chemistry. vol. 49, XP002500196, pp. 2875-2880 (1984).

Heitman, J., et al., "Targets for Cell Cycle Arrest by the Immunosuppressant Rapamycin in Yeast," Science, vol. 253, pp. 905-909, (1991).

Ho, "Hydrodenitrogenation catalysis," Catal. Rev. Sci. Eng., vol. 30, No. 1, pp. 117-160, (1988).

Kamm et al., "Biorefinery—Systems," Chem, Biochem. Eng, Q., vol. 18, No. 1, pp. 1-6, (2004).

Katho, A. et al., "Determination of Ornithine and Lysine by Visible Spectrophotometry," Analytical Letters, vol. 26, No. 1, pp. 73-86, (1993).

Kisfaludy, Lajos, et al., "One-step synthesis of L-piperidine-2-carboxylic acid," vol. 2, p. 163, (1982).

Lankey, R. L. and Anastas, P. T. (ed.), "Advancing Sustainability Through Green Chemistry and Engineering," ACS Symposium Series, 823, American Chemical Society, Washington, D.C., (2002).

Ledoux et al., "Hydrodenitrogenation activity and selectivity of well-dispersed transition metal sulfides of the second row on activated carbon," J. Catalysis, vol. 115, pp. 580-590, (1989).

Matsuguma et al., "Hydropxylamine-O-Sulfonic Acid," Inorganic Syntheses vol. 5, pp. 122-125, (1957).

Metelkina et al., "Reaction of metal alkoxides with lysine: substitution of alkoxide ligands vs. lactam formation," Monatshefte für Chemie, vol. 134, pp. 1065-1069, XP002348859, (2003).

Mochida et al., "An overview of hydrodesulfurization and hydrodenitrogenation," Japan Pet. Inst., vol. 47, No. 3, pp. 145-163, (2004).

Mosedale, D.E., et al., "Circulating levels of MCP-1 and eotaxin are not associated with presence of atherosclerosis or previous myocardial infarction, " Atherosclerosis., vol. 183, pp. 268-274, (2005).

Naidu, B.V., et al., "Broad-Spectrum Chemokine Inhibition Ameliorates Experimental Obliterative Bronchiolitis," The Annals of Thoracic Surgery, vol. 75, No. 4, pp. 1118-1122, (2003).

Ohtani, Bunsho, et al., "Titanium(IV) oxide photocatalyst of ultrahigh activity for selective N-cyclization of an amino acid in aqueous suspensions," Chemical Physical Letters, vol. 242, No. 3, pp. 315-319, (1995).

Ohtani, Bunsho, et al., "Photocatalytic Racemization of Amino Acids in Aqueous Polycrystalline Cadmium(II) Sulfide Dispersions," Journal of the Chemical Society, vol. 91, No. 7, XP000497529, pp. 1103-1109, Apr. 7, 1995.

Ohtani, Bunsho, et al., "Photocatalytic One-Step Syntheses of Cyclic Imino Acids by Aqueous Semiconductor Suspensions," Journal of Organic Chemistry, vol. 55, No. 21, XP002500194, pp. 5552-5553, (1990).

Pal, B., et al., "Photocatalytic redox-combined synthesis of L-pipecolinic acid from L-lysine by suspended titania particles: effect of noble metal loading on the selectivity and optical purity of the product," Journal of Catalysis, vol. 217, pp. 152-159, (2003).

Paruszewski, R., et al., "Amino acid derivatives with anticonvulsant activity," Chem. Pharm. Bull., vol. 49, pp. 629-631, (2001).

Pellegata et al., "An improved sysnthesis of γ-, δ-, and ε-lactams," Synthesis, pp. 614-616, (1978).

Ramamurthy et al., "An improved synthesis of carbon-14 labelled carboxylic acids from carbon-14 labelled amino acids," J. Labelled Compd. Rad., vol. 25, No. 8, pp. 809-814, (1988).

Reckless, J., et al., "Broad-Spectrum Chemokine Inhibition Reduces Vascular Macrophage Accumulation and Collagenolysis Consistent With Plaque Stabilization in Mice," Journal of Vascular Research, vol. 42, pp. 492-502, (2005).

Reckless, J., et al., "Identification of oligopeptide sequences which inhibit migration inducted by a wide range of chemokines.", Biochemistry Journal., vol. 15, pp. 340 (pt.3), p. 803-811, (1999).

Reckless, J., et al., "The pan-chemokine inhibitor NR58-3.14.3 abolishes TNF-alpha accumulation and leukocyte recruitment inducted by lipopolysaccharide in vivo," Immunology, vol. 103, pp. 244-254, (2001).

Rota et al., "Role of hydrogenolysis and nucleophilic substitution in hydrodenitrogenation over sulfided NiMo/y-Al2O3," J. Catalysis, vol. 202, pp. 195-199, (2001).

Rota et al., "Stereochemistry of hydrodenitrogenation: the mechanism of elimination of the amino group from cyclohexylamines over sulfided Ni-Mo/y-Al2O3 catalysts," J. Catalysis, vol. 200, pp. 389-399, (2001).

Schendel, Frederick J., et al., "Production at 50° C by Mutants of a Newly Isolated and Characterized Methylotrophic *Bacillus* sp," Applied and Environmental Microbiology, vol. 56, No. 4, pp. 963-970, (1990).

Schroff, R.W., et al., "The toxicology of chemokine inhibition," Mini-Reviews in Medicinal Chemistry, vol. 5, pp. 849-855, (2005).

Shuker, S.B., et al., "Discovering high-affinity ligands for proteins: SAR by NMR," Science, vol. 274, pp. 1531-1534, (1996).

Skerritt, J.H., et al., "Differential modulation of gamma-aminobutyric acid receptors by caprolactam derivatives with central nervous system depressant or convulsant activity," Brain Research, vol. 331, No. 2, pp. 225-233, (1985).

Takei, Go, et al., "Photocatalytic redox-combined synthesis with TiO2 film modified microchannel," Special Publication—Royal Society of Chemistry, vol. 1, pp. 93-95, (2004).

Thomsen et al., "Manufacturing of stabilised brown juice for L-lysine production—from university lab scale over pilot scale to industrial production," Chem. Biochem. Eng. Q., vol. 18, No. 1, pp. 37-46, (2004).

Vit et al., "Simultaneous hydrodenitrogenation of pyridine and hydrodesulfurization of thiophene over carbon-supported platinum metal sulfides," J. Catalysis, vol. 119, pp. 1-7, (1989).

Wilbert, S.M., et al., "Quantitative analysis of a synthetic peptide, NR58-3.14.3, in serum by LC-MS with inclusion of a diastereomer as internal standard," Analytical Biochemistry, vol. 278, No. 1, pp. 14-21, (2000).

Williams, M.F., "Sulfur and Nitrogen sensitivity of Supported Pt-Hydrogenation Catalysts," Doctoral Dissertation, Technische Universität München, (2005).

Zhang et al., "Aqueous-phase hydrogenation of lactic acid to porpylene glycol," Appl. Catal. A-Gen., vol. 219, pp. 89-98, (2001).

Zhang et al., "Kinetics of aqueous hydrogenation of lactic acid to propylene glycol," Ind. Eng. Chem. Res., vol. 41, pp. 691-696, (2002).

Zhao et al., "Investigation of the mechanism of the hydrodenitrogenation of n-hexylamines over sulfided NiMo/y-Al2O3," J. Catalysis, vol. 221, pp. 441-454, (2004).

Zhao et al., "Mechanisms of the hydrodenitrogenation of alkylamines with secondary and tertiary a-carbon atoms on sulfided NiMo/Al2O3," J. Catalysis, vol. 222, pp. 532-544, (2004).

Zhao, "Mechanisms of hydrodenitrogenation of amines over sulfided NiMo, CoMo, and Mo supported on Al2O3," (doctoral dissertation; Swiss Federal Institute of Technology, Zurich), http://e-collection.ethbib.ethz.ch/ecol-pool/diss/fulltext/eth15555.pdf(2004).

Chemistry Project, Synthesis and Characterisation of Novel (Acylamino) caprolactams, (2005).

International Preliminary Report on Patentability for International App. No. PCT/US2008/002202 (8 pages), (2008).

CATALYTIC DEAMINATION FOR CAPROLACTAM PRODUCTION

RELATED APPLICATIONS

This application is a national stage application of International Application No. PCT/US2008/002202 filed Feb. 20, 2008, which claims the benefit of and priority to U.S. patent application Ser. No, 60/902,211, filed on Feb. 20, 2007.

STATEMENT OF GOVERNMENT INTEREST

The present work was performed in part with funding from the U.S. National Science Foundation, Grant No. NSF CHE-0211375. The U.S. Government may have certain rights in this technology.

BACKGROUND

The present technology relates to routes for catalytic conversion of lysine or α-amino-ε-caprolactam to high value compounds that can be derivatized to prepare polymers, pharmaceuticals, and other useful materials.

Lysine is useful as a starting material for production of various azacyclic hydrocarbons. For example, lysine can be used to prepare α-amino-ε-caprolactam ("ACL"), which can then be deaminated to form epsilon-caprolactam, as described, e.g., in WO2005/123669 to Frost. Lysine can also be used to prepare pipecolinic acid ("PCA"), as described in B. Pal et al., Photocatalytic redox-combined synthesis of L-pipecolinic acid from L-lysine by suspended titania particles: effect of noble metal loading on the selectivity and optical purity of the product, *J. Catal.* 217:152-59 (2003) (available on-line at http://eprints.lib.hokudai.ac.jp/dspace/bitstream/2115/14649/1/JC2003-217-1.pdf).

Epsilon-caprolactam (hereinafter "caprolactam") is a high-value compound that is in widespread used for nylon-6 production and is also useful, e.g.: for preparation of other polyamides for synthetic fibers, films, and coatings; for preparation of pharmaceutical compounds such as CNS depressants, muscle relaxants, anti-hypertensives, and angiotensin converting enzyme inhibitors; and as a plasticizer or cross-linking agent for various polymers. See, e.g., U.S. Pat. No. 6,504,047 to Knaup; U.S. Pat. No. 4,520,021 to Harris et al.; and J. H. Skerritt et al., Differential modulation of gamma-aminobutyric acid receptors by caprolactam derivatives with central nervous system depressant or convulsant activity, *Brain Res.* 331(2):225-33 (8 Apr. 1985).

PCA is also useful to form various PCA derivatives that are high value pharmaceuticals, examples of which include viral protease inhibitors, anti-convulsants, analgesics, and biliary disorder treatments. See, e.g., US 2001/0056184 to Noda et al.; U.S. Pat. No. 5,807,870 to Anderson et al.; U.S. Pat. No. 5,639,744 to Marchi et al.; U.S. Pat. No. 4,826,819 Vecchietti et al.; J. Heitman et al., Targets for cell cycle arrest by the immunosuppressant rapamycin in yeast, *Science* 253:905-909 (23 Aug. 1991) [doi: 10.1126/science.1715094]; S. B. Shuker et al., Discovering high-affinity ligands for proteins: SAR by NMR, *Science* 274:1531-34 (29 Nov. 1996) [doi: 10.1126/science.274.5292.1531]; F. Couty, Asymmetric syntheses of pipecolic acid and derivatives, *Amino Acids* 16(3-4):297-320 (September 1999) (doi: 10.1007/BF01388174); and R. Paruszewski et al. Amino acid derivatives with anti-convulsant activity, *Chem. Pharm. Bull.* 49:629-31 (2001) (doi: 10.1248/cpb.49.629).

Additionally, because of their bioactive effects, caprolactam and PCA are also commonly used to prepare pharmaceutical candidate compounds, such as receptor and/or enzyme ligands. In some cases, the core of such a compound can comprise the caprolactam or PCA residue; in some cases a pendant moiety of the compound can comprise the caprolactam or PCA residue.

Employing readily obtainable, inexpensive lysine as a starting material offers the option of avoiding costly petrochemical synthesis of caprolactam. In regard to PCA, employing a lysine starting material provides the option of avoiding extensive purification steps for isolating commercial quantities of PCA from biological sources or for isolating large quantities of biological picolinic acid for reduction to PCA. Yet, to date there have been provided only a limited number of catalytic routes for converting lysine to such useful high-value materials. In particular, deamination of ACL has been described, but no routes utilizing hydrodenitrogenation has been identified.

Hydrodenitrogenation of petroleum has traditionally employed sulfided Co—Mo on $Al_2O_3$ and sulfided Ni—Mo on $Al_2O_3$. See, T. C. Ho, *Catal. Rev. Sci. Eng.* 1988:117-160; and I. Mochida et al., *Japan Pet. Inst.* 47:145-163 (2004). The amines in petroleum include heterocyclic amines, anilines, and aliphatic amines. Hydrodenitrogenations of substituted cyclohexylamines, other alkylamines, and substituted pyridine using sulfided Ni—Mo on $Al_2O_3$ have been mechanistically studied. See respectively: F. Rota et al., *J. Catalysis* 200:389-399 (2001) and F. Rota et al., *J. Catalysis* 202:195-199 (2001) (cyclohexylamines); Y. Zhao et al., *J. Catalysis* 222:532-544 (2004) and Y. Zhao et al., *J. Catalysis* 221:441-454 (2004) (other alkylamines); and M. Egorova et al., *J. Catalysis* 206:263-271 (2002) (substituted pyridine).

Gas phase hydrodenitrogenation of aliphatic amines, heterocyclic amines, and anilines have been reported using stoichiometric amounts of Pt on $SiO_2$. See M. J. Guttieri et al., *J. Org. Chem.* 49:2875-2880 (1984). Pyridine hydrodenitrogenation has been studied using C-supported sulfided NiMo, Zr, Ag, Nb, Mo, Rh, and Pd catalysts. See M. J. Ledoux et al., *J. Catalysis* 115:580-590 (1989). Simultaneous hydrodenitrogenation of pyridine and hydrodesulfurization of thiophene employed C-supported Rh, Ru, Pd, Ir, and Pt. See, e.g., Z. Vit et al., *J. Catalysis* 119:1-7 (1989). In addition, quinoline hydrodenitrogenation has been examined using sulfided, C-supported W, Re, Os, Ir, Pt, Mo, Ru, Rh, Pd, V, Cr, Mn, Fe, Co, and Ni. See S. Eijsbouts et al., *J. Catalysis* 109:217-220 (1988).

However, hydrodenitrogenation of L-lysine and alpha-aminocaprolactam have not been previously reported. Therefore, it would be advantageous to provide alternative and improved methods for converting inexpensive lysine starting materials to useful, high value products such as caprolactam, PCA, and their derivatives, by novel hydrodenitrogenation routes that can be practiced in a convenient one-pot reaction format.

SUMMARY

In various embodiments, the present technology provides alternative and improved methods for converting lysine or alpha-amino-caprolactam (ACL) starting materials to caprolactam, PCA, and their derivatives, by novel hydrodenitrogenation routes that can be practiced in a convenient one-pot reaction format. In various embodiments, the present technology further provides:

Processes for preparing a reaction product comprising caprolactam, such processes comprising the step of contacting a reactant comprising lysine, alpha aminocaprolactam, salts thereof, thereof with a catalyst, and a gas comprising hydrogen gas, the catalyst being optionally supported on a catalyst support, and optionally said contacting is performed in the presence of a solvent;

Processes for preparing caprolactam or a derivative thereof, involving: contacting a starting material comprising lysine or alpha-amino caprolactam (ACL), with a hydrodenitrogenation catalyst, in a solvent (e.g., an organic solvent), and contacting that combination with an $H_2$ gas or $H_2$ gas mixture atmosphere to form a reaction mixture; bringing the reaction mixture to an elevated temperature at which the hydrodenitrogenation reaction can proceed; and maintaining the reaction mixture at an elevated temperature for a sufficient time for the hydrodenitrogenation reaction to produce caprolactam;

Such processes in which the catalyst is a transition metal hydrodenitrogenation catalyst; such processes in which the hydrodenitrogenation catalyst comprises a sulfided transition metal; such processes in which an $H_2$ gas mixture atmosphere thereof comprises $H_2S$;

Such processes that further involve isolating caprolactam so produced, or preparing a derivative of caprolactam so produced, or both;

Processes for preparing pipecolinic acid or a derivative thereof, involving: contacting a starting material comprising lysine, with a hydrodenitrogenation catalyst, in a reaction solvent, and contacting that combination with an $H_2$ gas or $H_2$ gas mixture atmosphere to form a reaction mixture; bringing the reaction mixture to an elevated temperature at which the hydrodenitrogenation reaction can proceed; and maintaining the reaction mixture at an elevated temperature for a sufficient time for the hydrodenitrogenation reaction to produce pipecolinic acid;

Such processes in which the catalyst is a transition metal hydrodenitrogenation catalyst; such processes in which the reaction solvent comprises water;

Such processes that further involve isolating pipecolinic acid so produced, or preparing a derivative of pipecolinic acid so produced, or both;

Processes for preparing caprolactam, such processes comprising: heating a reactant comprising lysine to a temperature of about 50° C. to 300° C., optionally in the presence of a first catalyst to produce a first reaction product comprising alpha amino caprolactam; contacting said first reaction product with a gas comprising hydrogen and a second catalyst produce a second reaction product comprising caprolactam; and recovering caprolactam from the second reaction product to produce a recovered caprolactam;

Systems for preparation of caprolactam or a caprolactam derivative, in which the systems include (1) a starting material containing lysine or alpha-amino caprolactam (ACL), (2) a hydrodenitrogenation catalyst, (3) an organic hydrodenitrogenation reaction solvent, and (4) $H_2$ gas or an $H_2$ gas mixture; wherein a combination of (1), (2), and (3), under an atmosphere of (4), is capable upon heating of producing caprolactam by hydrodenitrogenation of the lysine or ACL;

Systems for preparing pipecolinic acid or a pipecolinic acid derivative, in which the systems include (1) a starting material containing lysine, (2) a hydrodenitrogenation catalyst, (3) an aqueous reaction solvent, and (4) $H_2$ gas or an $H_2$ gas mixture; wherein a combination of (1), (2), and (3), under an atmosphere of (4), is capable upon heating of producing pipecolinic acid by hydrodenitrogenation of the lysine or ACL; and Caprolactam and caprolactam derivatives produced thereby; and pipecolinic acid and pipecolinic acid derivatives produced thereby.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary,") and sub-headings (such as "Starting Materials") used herein are intended only for general organization of topics within the disclosure of the technology, and are not intended to limit the disclosure of the technology or any aspect thereof. In particular, subject matter disclosed in the "Introduction" may include aspects of technology within the scope of one or more inventions, and may not constitute a recitation of prior art. Subject matter disclosed in the "Summary" is not an exhaustive or complete disclosure of the entire scope of the technology or any embodiments thereof.

The citation of references herein does not constitute an admission that those references are prior art or have any relevance to the patentability of the technology disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific Examples are provided for illustrative purposes of how to make, use and practice the compositions and methods of this technology and, unless explicitly stated otherwise, are not intended to be a representation that given embodiments of this technology have, or have not, been made or tested.

In various embodiments hereof, catalytic hydrodenitrogenation of α-aminocaprolactam or lysine are performed to provide caprolactam, or in some lysine-utilizing embodiments pipecolinic acid. In some embodiments, L-lysine can be used as a starting material, and this can be derived from a simple carbon source, as illustrated in Scheme 1.

Scheme 1

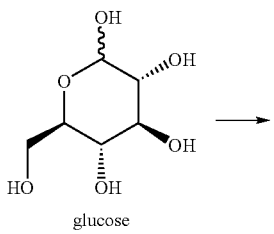

glucose

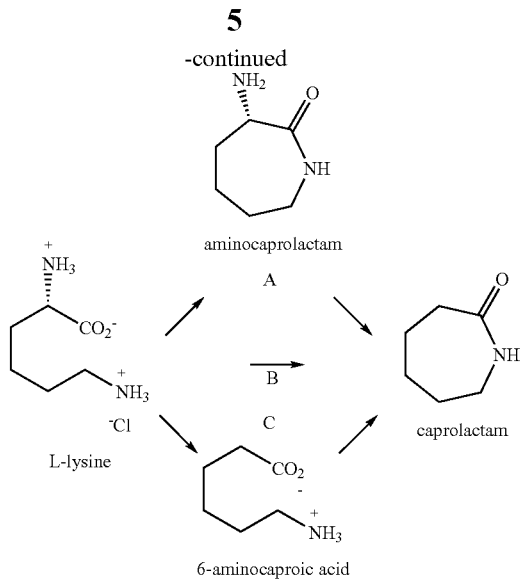

As shown in Scheme 1, three routes can be contemplated for conversion of L-lysine to caprolactam. The route labeled "A" proceeds via ACL, "B" proceeds directly to caprolactam, and "C" through 6-aminocaproic acid.

Thus, in various embodiments according to the present technology, lysine, e.g., D-, L-, or racemic lysine, can be converted to caprolactam or to pipecolinic acid (PCA), in a one-pot reaction. In various embodiments hereof, α-amino-ε-caprolactam (ACL), e.g., D-, L-, or racemic ACL, can be converted to caprolactam in a one-pot reaction. These conversions are performed using hydrodenitrogenation conditions and catalysts.

Starting Materials

As described in WO2005/123669 to Frost, various routes can be used to provide lysine; for example, a simple carbon source can be bioconverted to lysine. Also as described therein, lysine can be cyclized to form α-aminocaprolactam (ACL). Such routes are useful to provide starting materials for reactions according to various embodiments of the present technology. Various commercial sources of lysine or ACL are also useful. In some embodiments, the lysine or ACL can be L-lysine or L-ACL.

Starting materials can comprise the lysine or ACL, as well as other components that do not inhibit the reaction. Thus, either neat or raw or partially purified lysine or ACL sources can be used in various embodiments. Starting materials can comprise solvent(s), buffer(s), free radical scavengers, and other components that enhance or do not inhibit the catalyzed reaction(s).

Catalysts

A reaction hereof utilizes a hydrodenitrogenation catalyst. Various hydrodenitrogenation catalysts can be used, such as are known in the art. Common examples of these include: (1) transition metal compounds, e.g., oxides, carbides; and (2) transition metals and their alloys. In various embodiments hereof, the selected hydrodenitrogenation catalyst can be a transition metal hydrodenitrogenation catalyst or a transition metal combination or alloy hydrodenitrogenation catalyst. Among transition metal and alloy hydrodenitrogenation catalysts, those comprising a Group IB, Group VB, Group VIB, Group VIIB, or Group VIIIB transition metal are considered desirable; in various embodiments the catalyst can comprise a Group VIB, Group VIIB, or Group VIIIB transition metal, or Au; in some embodiments, the catalyst can comprise a Group VIIB or Group VIIIB transition metal, or Au.

In some embodiments, a noble metal or a Mo or Mo alloy/combination catalyst can be used. Useful examples of these include Pt, Au, Pd, Rh, Re, Ru, and Ir; and Ni—Mo and Co—Mo alloys. In some embodiments, a Ni metal catalyst can be used. In reactions converting lysine to pipecolinic acid, Ni metal catalysts are also useful; in some embodiments thereof, the catalyst can be Raney nickel. In some embodiments of lysine to pipecolinic acid conversions hereof, the catalyst can comprise Au, Pd, Rh, Re, Ru, Ir, or Ni.

Further catalysts useful herein include those described, e.g., in: M. F. Williams, "Sulfur and Nitrogen Sensitivity of Supported Pt-Hydrogenation Catalysts" (June 2005) (doctoral dissertation; Technische Universität München) (available on-line at http://deposit.ddb.de/cgi-bin/dokserv?idn=97769531x&dok_var=d1&dok_ext=pdf&filename=97769531x.pdf); Y. Zhao, "Mechanisms of Hydrodenitrogenation of Amines over Sulfided NiMo, CoMo, and Mo Supported on $Al_2O_3$," (2004) (doctoral dissertation; Swiss Federal Institute of Technology, Zurich) (available on-line at http://e-collection.ethbib.ethz.ch/ecol-pool/diss/fulltext/eth15555.pdf); U.S. Pat. No. 4,368,115 to Chianelli et al. for "Catalysts comprising layered chalcogenides of group IVb-group VIII) prepared by a low temperature nonaqueous precipitate technique;" and U.S. Pat. Nos. 5,252,199 and 5,278,121 to Singhal et al. respectively for "Hydrotreating process using novel multimetallic sulfide catalysts," and for "Multimetallic sulfide catalyst containing noble metals for hydrodenitrogenation."

In some embodiments, the metal or alloy hydrodenitrogenation catalyst can be sulfided prior to use, as by contact at elevated temperature with $H_2S$ gas, e.g., an $H_2/H_2S$ mixture; in some embodiments, the sulfiding can be performed using catalyst material from which much or all of the adsorbed oxygen and/or nitrogen has been removed, e.g., such as by flushing with a noble gas.

The catalyst(s) used in a reaction hereof can be provided as particles, e.g., microparticles or nanoparticles, or in the form of a monolithic or porous solid, or in any format that presents at least one contiguous surface area of the catalytic species, e.g., a nano-textured noble metal surface. The catalyst can be presented on a solid support in various embodiments. In embodiments in which a catalyst support is used, the support can be any useful support known in the art. Such support materials include: carbon; $SiO_2$; metal(s); alloy(s); and metal compound(s), e.g., metal salts, carbides, or oxides, such as NiO, $Al_2O_3$, $TiO_2$, $ZrO_2$, aluminosilicates, silica-titania, titania-alumina, and mixed oxides (e.g., Ti—Zr—V mixed oxides), and the like, and mixtures thereof.

Support particles can be of any morphology, e.g., substantially ellipsoidal or n-hedral (e.g., 3<n<25). Fiber and whisker embodiments are also useful in some embodiments. In various embodiments, a support can be a macroporous or microporous solid, such as a zeolite or other molecular sieve, or a macroporous solid whose pores have a cross-sectional honeycomb or other geometry. In some embodiments hereof, the support comprises carbon particles, silica particles, or NiO particles.

The catalytic species can be deposited on the support utilizing any of the various methods known useful therefore in the art, such as by sputter-coating, or by deposition involving heating an aqueous solution of a salt of the metal species with which solution the support material is in contact. In embodiments that employ heating a metal salt solution, metal halides, e.g., metal chlorides, can be used, examples of which include $H_2PtCl_6$ and $HAuCl_4$.

Reaction Conditions

In various embodiments, a hydrodenitrogenation reaction hereof involves combining the lysine or ACL starting material with a hydrodenitrogenation catalyst in hydrodenitrogenation reaction solvent. The resulting combination is placed under an atmosphere of $H_2$ gas or an $H_2$ gas mixture to form a reaction mixture. The reaction mixture is typically located within a reaction vessel; and in various embodiments, the reaction vessel can be one that is able to withstand charging with pressures up to, e.g., about 1000 psi, about 5000 psi, or more. Glass and stainless steel vessels are commonly employed; and reaction vessels can be lined with a layer of, e.g., a glass, PTFE, PHFP, PFEP (e.g., TEFLON), or other non-reactive substance.

In hydrodenitrogenation reactions hereof that are employed for producing caprolactam, the reaction solvent can be an organic reaction solvent. In some embodiments, an organic reaction solvent can be chosen from among tetrahydrofuran (THF), dimethylformamide (DMF), chlorobenzene, chloroform, pyridine, and combinations thereof. In some embodiments, THF can be used as the organic reaction solvent. In some embodiments, in which the conversion of lysine to caprolactam is catalyzed, the reaction solvent can be ethanol.

In the case of conversion of lysine to pipecolinic acid, the reaction solvent can be aqueous, e.g., water.

The atmosphere in the reaction vessel can comprise $H_2$ or an $H_2$-and-$H_2S$ mixture. Where an $H_2/H_2S$ mixture is used, the $H_2S$ can be present as a minority component, i.e. less than 50 vol. % and about or at least 1 vol. % of the total gas content of the atmosphere. In some embodiments, about or at least 5 vol. %, or about or at least 10 or 15 vol. %, $H_2S$ can be present. In some embodiments, about or up to 40 vol. %, or up to or about 35 or 30 vol. % $H_2S$ can be present. In various such embodiments, from about 5 to about 40 vol. % $H_2S$ can be present, or from about 5 to about 30, or from about 5 to about 25, or from about 10 to about 25, or about 20 vol. %.

The pressure of the reaction vessel atmosphere can be elevated. In some embodiments, at the start of the reaction, the pressure can be from about 50 to about 3000 psi, or from about 100 to about 1000 psi, or up to about 500 or 200 or 250 psi; in some embodiments, the pressure can be from about 50 to about 150 psi. In reactions in which the reaction vessel is charged with about 50 to about 150 psi of gas, during the reaction the temperature typically rises to about 600 to 650 psi.

In various embodiments, the reaction mixture is heated and maintained at an elevated temperature at which hydrodenitrogenation reaction can proceed. In various embodiments, the elevated temperature can be at least or about 100° C., but is kept below a temperature at which either the reaction cannot proceed or at which the reactants or products are combusted or otherwise unrecoverably destroyed. In some embodiments, the elevated temperature can be from about 50° C. to about 300° C., or from about 200° C. to about 300° C., or about 250° C.

In performing the reaction, the starting material containing lysine or ACL is contact with the catalyst in a reaction solvent; and this combination is placed under (i.e. contacted with) an atmosphere as described above; this statement is used herein to indicate that the combination can be contacted with such an atmosphere as a separate step or can be prepared under the stated atmosphere. This does not limit the reaction to use in batch formats.

A variety of different reaction formats are useful herein. Though batch reaction processes can be used, continuous and fed-batch formats are also useful, as are extractive formats in which the desired products and/or targeted by-products are removed from the reaction mixture either intermittently or continuously. Stirred tank, reflux, and other circulation formats can likewise be employed. These and other useful reaction formats and, where mixing is desired, mixing modes, are well known in the field of art and any such techniques known useful therefore can be employed.

In various embodiments, the reaction mixture remains above room temperature, or is maintained at the desired elevated temperature, for a sufficient time to permit the reaction to proceed. In various embodiments, such a reaction time can be from about 0.1 to about 12 hours, or from about 1 to about 10, or about 2 to about 8 hours, or from about 4 to about 8 hours.

After a given reaction, the desired product can be recovered. Also, the catalyst can be re-used. In some embodiments, a caprolactam or pipecolinic acid product can be further treated to produce a derivative thereof. The caprolactam or pipecolinic acid used to prepare such a derivative can, in some embodiments, first be recovered from the reaction mixture, e.g., by separation, to any desired degree of purity.

Further materials and methods useful in various embodiments hereof are known to one of ordinary skill in the art. Some sources of useful materials and methods include: T. C. Ho, *Catal. Rev. Sci. Eng.* 1988:117-160; I. Mochida et al., *Japan Pet. Inst.* 47:145-163 (2004); F. Rota et al., *J. Catalysis* 200:389-399 (2001); F. Rota et al., *J. Catalysis* 202:195-199 (2001); Y. Zhao et al., *J. Catalysis* 222:532-544 (2004); Y. Zhao et al., *J. Catalysis* 221:441-454 (2004); M. Egorova et al., *J. Catalysis* 206:263-271 (2002); M. J. Guttieri et al., *J. Org. Chem.* 49:2875-2880 (1984); M. J. Ledoux et al., *J. Catalysis* 115:580-590 (1989); Z. Vit et al., *J. Catalysis* 119: 1-7 (1989); S. Eijsbouts et al., *J. Catalysis* 109:217-220 (1988); M. S. Chen et al., *Science* 306:252-255 (2004); and A. Corma et al., *Science* 313:332-334 (2006).

Further Embodiments

As stated above, various reaction formats hereof can employ different orders of addition of reaction materials (reactants, solvents, gases), catalysts, and other components to a reactor, for performing a catalytic hydrodenitrogenation reaction according to various embodiments hereof, using a starting material that comprises lysine or alpha-amino caprolactam (ACL).

Hydrodenitrogenation catalysts that can be employed herein include any known useful therefore in the art, common examples of which include those comprising Group VIB metals, such as: Mo, Ni—Mo, Co—Mo, W, Ni—W, Co—W catalysts; catalysts comprising one or more such metal(s); and sulfides, phosphides, nitrides, carbides, or borides of any of the foregoing, e.g., $MoS_2$, MoP, MoN, $Mo_2C$, WP, NiP, CoMoP, NiMoP, and the like. Combinations thereof can be used in some embodiments. In some embodiments, transition metal oxide(s) can be used as alternative or supplemental catalysts. In some embodiments the catalyst can further comprise one or more additional transition metals in combination with the above-described materials. In some embodiments, a non-transition-metal promoter such as barium can be included in or with the catalyst. Any method known in the art as useful therefore can be applied to prepare the selected catalyst(s).

Typically, the selected catalyst is provided disposed on a solid support such as alumina, silica, titania, or other inert material, and this can be an amorphous or structured material, e.g., having a zeolite, honeycomb, or other structure. The supported catalyst can be provided in the form of a porous or monolithic solid mass for a fixed bed reactor, or in any desired particulate or other format useful for a stirred tank, moving bed, fluid bed, floating bed, rolling bed, or other desired reactor geometry. In some embodiments, catalyst combinations can be used, e.g., with different catalysts occupying different micro, meso, or macro zones of the reactor. Multi-bed reactors can be used in some embodiments hereof. In some multi-bed reactor embodiments, each bed can comprise the same catalyst or catalyst combination or a different catalyst or catalyst combination. Different catalysts can be prepared using the same or different solid support materials; and, similarly, differently supported versions of the same catalyst can be used in some embodiments hereof.

The reaction conditions of various embodiments hereof typically employ a reaction solvent, which is commonly an organic reaction solvent. In various embodiments, examples of useful organic reaction solvents include hydrocarbons of up to or about C18, typically about C5 to about C16, or about C6 to about C10. In some embodiments, the solvent can be a homohydrocarbon solvent. The solvent can be aliphatic, cycloaliphatic, or aromatic. In some embodiments that employ an aliphatic or cycloaliphatic solvent, the solvent can be saturated. Examples of common useful solvents include: hexane, octane, decane, hexadecane, cyclohexane, benzene, and toluene, and combinations thereof.

The reaction materials hereof include, in addition to the to-be-hydrodenitrogenated compound, a gas comprising $H_2$. In some embodiments, the gas can comprise a mixture of $H_2$ with one or more additional gases, e.g., inert gases, or gases useful for maintaining the catalyst. For example, in some embodiments in which a sulfided catalyst is used, $H_2S$ can be included in the gas.

In various embodiments, the reaction conditions useful for catalytic hydrodenitrogenation processes hereof include elevated pressure and elevated temperature, i.e. elevated above ambient conditions of about 25-45° C. and about 0.1 MPa. In some embodiments, a total elevated reaction pressure of, typically, up to or about 20 MPa can be used, and this can be at least or about 0.5, 1, 2, 3, 5, 10, or 15 MPa, or less than or about 15, 10, or 5 MPa; a typical pressure can fall within a range from about 2 to about 10 MPa, or from 2 to about 5 MPa. In some embodiments, the temperature can be from about 175 to about 500° C., and this can be at least or about 200, 250, or 300° C., and less than or about 500, 450, 400, 350, or 300° C.; a typical temperature can fall within a range of about 250 to about 500° C., about 250 to about 450° C., about 250 to about 400° C., or about 250 to about 350° C.

Further examples of catalysts, solvents, reaction conditions, and reactor geometries for hydrodenitrogenation processes useful herein, include those described, e.g., in U.S. Pat. No. 4,022,683 to Bludis et al., U.S. Pat. No. 4,465,790 to Quayle, U.S. Pat. No. 4,716,142 to Laine et al., U.S. Pat. No. 4,740,487 to Matheson et al., U.S. Pat. No. 5,409,600 to Weissman et al., U.S. Pat. No. 5,855,767 to Powers et al., U.S. Pat. No. 6,162,351 to Sudhakar et al., U.S. Pat. No. 6,267,874 to Iijima et al., and U.S. Pat. No. 7,112,312 to Chou, all incorporated by reference herein.

In regard to orders of addition, in various embodiments, the selected catalyst can be loaded into the reactor before addition of the reaction materials, or the reaction materials can be added to the reactor before addition of the catalyst, although the former types of formats are considered particularly useful in some embodiments hereof. Similarly, where the gas and other reaction materials are mixed together before admission to the reactor, each of these can be heated before being mixed, or they can be mixed first and then heated, although latter formats can be particularly useful in some embodiments hereof. Any materials added to the reactor can likewise be either preheated or non-preheated.

In some embodiments, the compound(s) to be hydrodenitrogenated can be gasified prior to admission to the reactor, or a liquid comprising such compound(s), e.g., along with reaction solvent, can be gasified prior thereto. This can typically be accomplished by pre-heating to about 240 or 250° C.

In some embodiments, the gas comprising $H_2$ or comprising $H_2$ and a supplemental gas, e.g., $H_2S$, can be provided to the reactor before addition of the to-be-hydrodenitrogenated compound, compound-comprising liquid, or gasified version thereof; in some embodiments, the gas and liquid can be combined to form a mixture of reaction materials, prior to being admitted to the reactor. In embodiments in which the gas is admitted to the reactor before addition of the compound to be hydrodenitrogenated, the reactor can contain the catalyst and reaction solvent, as well; and in some embodiments, such a loaded reactor can be brought to operating temperature and pressure, i.e. at which the hydrodenitrogenated reaction can proceed, prior to admission of the to-be-hydrodenitrogenated compound, compound-comprising liquid, or gasified version thereof. A liquid comprising the compound to be hydrodenitrogenated can comprise reaction solvent along with said compound(s), and this solvent can be in addition to reaction solvent that can already be present in the reactor. Where reaction solvent is present both pre-loaded into the reactor and in combination with the compound for hydrodenitrogenation, these can be the same or different reaction solvents, although normally the same solvent is selected.

In some embodiments, the reaction materials can be placed into the reactor and then heated, or can be pre-heated; and in some embodiments, the reactor can be pre-heated prior to addition of the reaction materials. Although it is possible to mix the catalyst, and the reaction material(s), i.e. either the liquid or liquid-gas mixture, before addition of the resulting catalyst-containing combination to the pre-heated or non-preheated reactor for heating, other embodiments, such as those in which a pre-heated or non-preheated liquid (or gasified liquid) or liquid-gas mixture of reaction materials is added to a catalyst-containing reactor is typically chosen.

In various embodiments, the reaction materials, i.e. either the liquid comprising the compound to be hydrodenitrogenated or the mixture thereof with the gas comprising $H_2$, can be preheated to about or at least a temperature in the range of 200 to 250° C. In some embodiments, the reaction materials are pre-heated to obtain a homogeneous gas phase that is then admitted to a reactor that already contains the catalyst. The reactor can also be a pre-heated reactor. Because the hydrodenitrogenated reaction is exothermic, the reactor temperature is commonly controlled to maintain the temperature within a desired elevated temperature range, typically within a range of about 250 to about 500° C., or about 300 to about 450° C.

Thus, some embodiments hereof can employ a process for preparing caprolactam or a derivative thereof, involving: (A) providing a reaction mixture comprising (1) a starting material comprising lysine or alpha-amino caprolactam (ACL), (2) a hydrodenitrogenation catalyst, (3) an organic reaction solvent, and (4) $H_2$ gas or an $H_2$ gas mixture, the mixture being at an elevated temperature at which a hydrodenitrogenation reaction can proceed; and (B) maintaining the reaction mixture at an elevated temperature for a sufficient time for the hydrodenitrogenation reaction to produce caprolactam.

Some embodiments hereof can involve: (A) providing (1) a starting material comprising lysine or alpha-amino caprolactam (ACL), (2) a hydrodenitrogenation catalyst, (3) an organic reaction solvent, and (4) $H_2$ gas or an $H_2$ gas mixture; (B) placing the starting material into contact with the catalyst, in the solvent, under an atmosphere of the gas or gas mixture, to form a reaction mixture; (C) bringing the reaction mixture to an elevated temperature at which the hydrodenitrogenation reaction can proceed; and (D) maintaining the reaction mixture at an elevated temperature for a sufficient time for the hydrodenitrogenation reaction to produce caprolactam.

Some such embodiments can involve: (A) providing (1) a starting material comprising lysine or alpha-amino caprolactam (ACL), (2) a hydrodenitrogenation catalyst, (3) an organic reaction solvent, and (4) $H_2$ gas or an $H_2$ gas mixture; (B) placing the starting material into contact with the catalyst, in the solvent, and placing the resulting combination under an atmosphere of the gas or gas mixture, to form a reaction mixture; (C) bringing the reaction mixture to an elevated temperature at which the hydrodenitrogenation reaction can proceed; and (D) maintaining the reaction mixture at an elevated temperature for a sufficient time for the hydrodenitrogenation reaction to produce caprolactam.

Some embodiments hereof can involve: (A) providing (1) a starting material comprising lysine or alpha-amino caprolactam (ACL), (2) a hydrodenitrogenation catalyst, (3) an organic reaction solvent, and (4) $H_2$ gas or an $H_2$ gas mixture; (B) placing the starting material into contact with the solvent and the gas or gas mixture, to form a reaction mixture; (C) bringing the reaction mixture to an elevated temperature at which the mixture is converted to a homogeneous gas; (D) placing the resulting homogeneous gas reaction mixture into contact with the catalyst at an elevated temperature at which the hydrodenitrogenation reaction can proceed; and (E) maintaining the reaction mixture at an elevated temperature for a sufficient time for the hydrodenitrogenation reaction to produce caprolactam.

EXAMPLES

General. A LAB-LINE HEET-CAB oven (Model No. 3515) is used for drying catalyst at constant temperature. The quartz U-tube reactor is situated inside of a temperature programmable Barnstead Thermolyne Furnace (Model No F6020C). Hydrodenitrogenations employ a Parr 4575 high pressure reactor and a Parr 4842 controller. To determine the concentration of pipecolinic acid and caprolactam, crude residue concentrate is dissolved in $D_2O$, concentrated to dryness, and then dissolved in 1 mL $D_2O$ containing 10 mM sodium 3-(trimethylsilyl)propionate-2,2,3,3-$d_4$ (TSP, δ 0.0 ppm).

Concentrations are determined by comparison of an integrated $^1H$ NMR resonance corresponding to pipecolinic acid and caprolactam with the integrated $^1H$ NMR resonance corresponding to TSP (δ 0.0). A standard calibration curve is individually determined for pipecolinic acid and caprolactam using solutions of known concentrations prepared from authentic samples of pipecolinic acid and caprolactam. The following resonances are used to quantify each molecule: pipecolinic acid (δ 2.96, dd, 1H); caprolactam (δ 2.46, m, 2H).

Hydrodenitrogenation of L-Lysine in Water. L-Lysine hydrochloride (1.83 g, 10 mmol), water (100 mL) and Raney Ni (0.58 g, 10 mmol) are added to the reaction chamber of a Parr high-pressure reactor and the vessel is assembled. The reaction chamber is flushed for 10 min with Ar and then pressurized with $H_2$ to 100 psi (689.48 kPa). The reaction chamber's outlet valve is then opened to the atmosphere. This process is repeated two additional times. After repressurizing the reaction vessel with 100 psi of $H_2$, the temperature of the stirred reaction vessel is increased to 200° C., which results in a reaction pressure of 300 psi. The reaction is held at 200° C. for 8 h. Upon cooling to rt (room temperature), the pressurized reaction vessel's $H_2$ is vented in a fume hood. After filtration, the reaction solution is concentrated.

Preparation of Pt—S/C. Activated C (8.37 g, 698 mmol) is mixed with $H_2PtCl_6.6H_2O$ (4.30 g, 8.3 mmol) and water (200 mL) and heated for 1 h at 90° C. The water is then removed under reduced pressure. The resulting solid is dried in an oven for 12 h at 80° C. After transferring to a quartz U-tube reactor in a temperature programmable furnace, the catalyst is heated from rt to 130° C. (heating rate: 5 C.° $min^{-1}$) under He (flow rate: 100 mL $min^{-1}$) and heated at this temperature for 1 h. The gas entering the quartz U-tube reactor is switched to $H_2/H_2S$ (10:1) (flow rate: 100 mL $min^{-1}$) and the temperature increased to 400° C. (heating rate: 5 C.° $min^{-1}$) and held at 400° C. for 2 h. The reactor is subsequently cooled to rt under He (flow rate: 100 mL $min^{-1}$) and the sulfided catalyst (Pt—S/C) stored under Ar. During the presulfiding process, the gas flowing out of the outlet of the quartz U-tube reactor is bubbled through a bleach solution to quench the $H_2S$ in a fume hood.

Preparation of Au—S/NiO. The support NiO (6 g, 80 mmol) is added to a 600 mL aqueous solution of $HAuCl_4$ (0.86 g, 2.52 mmol) and urea (15.12 g, 252 mmol). The suspension is vigorously stirred at 80° C. for 4 h resulting in the solution changing from pH 2 to pH 8. The mixture of $HAuCl_4$ and NiO is recovered by centrifugation (15000 g for 10 min), resuspended in 600 mL water, and centrifuged again. This water wash followed by centrifugation is repeated 4×. The washed mixture of $HAuCl_4$ and NiO is dried under vacuum at 100° C. for 2 h and transferred to a quartz U-tube reactor in a temperature programmable furnace and heated from rt to 100° C. (heating rate: 2 C.° $min^{-1}$) under He (flow rate: 80 mL $min^{-1}$). The gas is then switched to $H_2/H_2S$ (10:1) (flow rate: 80 mL $min^{-1}$) and the temperature increased to 300° C. (heating rate: 2 C.° $min^{-1}$) and held at 300° C. for 2 h. The reactor is cooled to rt under He (flow rate: 100 mL $min^{-1}$) and the sulfided catalyst ($HAuCl_4$—S/NiO) stored under Ar. During the presulfiding process, the gas outlet of the quartz U-tube reactor is bubbled through a bleach solution to quench the $H_2S$ in a fume hood.

Catalytic Hydrodenitrogenation of α-Amino-ε-caprolactam. Under Ar, α-amino-ε-caprolactam (1.28 g, 10 mmol), THF (100 mL) and 16.3 wt % Pt—S/C (0.8 mmol) are added to the reaction chamber of a Parr high-pressure reactor and the vessel is assembled. The reaction chamber is flushed for 10 min with Ar and then pressurized with $H_2/H_2S$ (5:1) to 100 psi. The reaction chamber outlet valve is then opened to the atmosphere. This process is repeated two additional times. After repressurizing the reaction vessel with $H_2/H_2S$ (5:1) to 100 psi, the temperature of the stirred reaction vessel is increased to 250° C., which results in a reaction pressure of 650 psi. The stirred reaction vessel is held at to 250° C. for 8 h. Upon cooling to rt, the pressurized reaction vessel's $H_2/H_2S$ atmosphere is vented through a bleach solution in a fume hood. After filtration, the reaction solution is concentrated, and the residue dissolved in EtOAc. The EtOAc solution is extracted with water followed by stirring the aqueous layer with activated carbon. Filtration and concentration affords crude caprolactam.

Direct Conversion of L-Lysine into Caprolactam. Under Ar, L-lysine hydrochloride (1.83 g, 10 mmol), NaOH (0.4 g, 10 mmol), EtOH (100 mL) and 16 wt % Pt—S/C (0.12 g, 0.1 mmol) are added to the reaction chamber of a Parr high-pressure reactor and the vessel is assembled. The reaction chamber is flushed for 10 min with Ar and then pressurized with $H_2/H_2S$ (10:1) to 100 psi. The reaction chamber outlet valve is then opened to the atmosphere. This process is repeated two additional times. After repressurizing the reaction vessel with $H_2/H_2S$ (10:1) to 150 psi, the temperature of the stirred reaction vessel is increased to 250° C., which results in a reaction pressure of 600 psi. The stirred reaction vessel is held at to 250° C. for 8 h. Upon cooling to rt, the pressurized reaction vessel's H₂/H₂S (10:1) atmosphere is vented through a bleach solution in a fume hood. After filtration, the reaction solution is concentrated to afford crude caprolactam.

Example 1

Hydrodenitrogenation of L-Lysine to Pipecolinic Acid

Hydrodenitrogenation of L-lysine is performed in water, using as a catalyst: Raney Ni, Ru on C, or Pd on C, under different water pressures. Although 6-aminocaproic acid is reasonably expected to form, catalytic hydrodenitrogenation is found to afford pipecolinic acid and no detectable 6-aminocaproic acid, according to the following reaction:

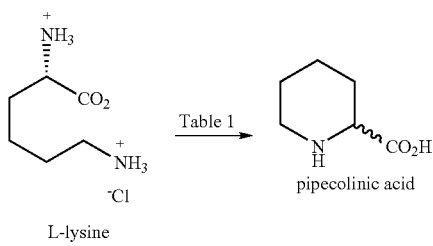

Results are shown in Table 1.

TABLE 1

Hydrodenitrogenation of L-Lysine in Water

| Entry | Catalyst | Temperature (° C.) | H₂ (psi) | Reaction time (h) | % Yield |
|---|---|---|---|---|---|
| 1 | Raney Ni | 200 | 100 | 8 | 33 |
| 2 | Raney Ni | 200 | 1000 | 8 | 65 |
| 3 | Ru on C[1] | 200 | 100 | 8 | 65 |
| 4 | Ru on C[1] | 200 | 1000 | 8 | 18 |
| 5 | Pd on C[1] | 200 | 100 | 8 | 43 |
| 6 | Pt on C[1] | 200 | 100 | 8 | 0 |

[1] 5 mol %

This shows that transition metal hydrodenitrogenation catalysts can be used to convert lysine to pipecolinic acid in a one-pot reaction in relatively high yields.

Example 2

Hydrodenitrogenation of ACL to Caprolactam

Hydrodenitrogenation of alpha-amino-caprolactam (ACL) is attempted, utilizing a variety of catalysts and conditions according to the following reaction.

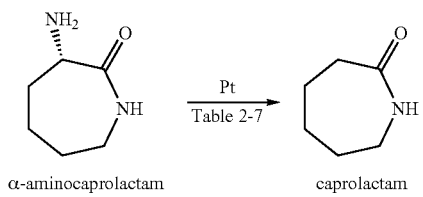

Initial attempts focus on hydrodenitrogenations in tetrahydrofuran (THF) catalyzed by Pt on C versus presulfided Pt on C and use of H₂ versus H₂/H₂S atmospheres (Table 2). An increase in the yield of caprolactam is observed when Pt is presulfided (entry 3 vs. entry 1, Table 2) and when an H₂/H₂S atmosphere is used (entry 2 vs. entry 1, entry 4 vs. entry 3, Table 2). Combination of both catalyst presulfidation and an H₂/H₂S atmosphere gives the highest yield of caprolactam produced from α-aminocaprolactam (entry 4, Table 2).

TABLE 2

Pt Sulfiding

| Entry | Catalyst (8 mol %) | Temperature (° C.) | H₂/H₂S (psi/psi) | Reaction time (h) | % Yield |
|---|---|---|---|---|---|
| 1 | Pt/C | 250 | 100/0 | 8 | 19 |
| 2 | Pt/C | 250 | 80/20 | 8 | 24 |
| 3 | Pt—S/C | 250 | 100/0 | 8 | 34 |
| 4 | Pt—S/C | 250 | 80/20 | 8 | 65 |

Use of sulfided Pt on C (Pt—S/C) as the catalyst, temperature, and reaction time are held constant while the H₂/H₂S atmosphere is varied (Table 3). An initial atmosphere of 80 psi/20 psi; H₂/H₂S is determined (entry 3, Table 3) to be the best mixture.

TABLE 3

H₂/H₂S atmosphere, Pt—S/C

| Entry | Catalyst (8 mol %) | Temperature (° C.) | H₂/H₂S (psi/psi) | Reaction time (h) | % Yield |
|---|---|---|---|---|---|
| 1 | Pt—S/C | 250 | 95/5 | 8 | 58 |
| 2 | Pt—S/C | 250 | 90/10 | 8 | 60 |
| 3 | Pt—S/C | 250 | 80/20 | 8 | 65 |
| 4 | Pt—S/C | 250 | 60/40 | 8 | 52 |

Presulfided Pt catalyst, reaction time, and the H₂/H₂S atmosphere are kept constant while temperature is varied (Table 4). This leads to 250° C. (entry 3, Table 4) being used as the routine hydrodenitrogenation reaction temperature.

TABLE 4

Temperature, Pt—S/C

| Entry | Catalyst (8 mol %) | Temperature (° C.) | H₂/H₂S (psi/psi) | Reaction time (h) | % Yield |
|---|---|---|---|---|---|
| 1 | Pt—S/C | 210 | 80/20 | 8 | 38 |
| 2 | Pt—S/C | 230 | 80/20 | 8 | 46 |
| 3 | Pt—S/C | 250 | 80/20 | 8 | 65 |
| 4 | Pt—S/C | 270 | 80/20 | 8 | 36 |
| 5 | Pt—S/C | 290 | 80/20 | 8 | 20 |

Prior to optimization of the initial H₂/H₂S atmosphere and the mol % catalyst of presulfided Pt (Pt—S/C) employed, a range of solvents is examined (Table 5). No formation of caprolactam is observed using acetonitrile (entry 1, Table 5) as solvent. The highest yield of caprolactam is achieved using THF (entry 2, Table 5). Use of 2,5-dimethyltetrahydrofuran (entry 3, Table 5) results in a tenfold reduction in the yield of caprolactam relative to use of THF as solvent (entry 3 vs. entry 2, Table 5).

TABLE 5

Solvent, Pt—S/C[1]

| Entry | Catalyst (4 mol %) | Solvent | $H_2/H_2S$ (psi/psi) | % Yield |
|---|---|---|---|---|
| 1 | Pt—S/C | acetonitrile | 135/15 | 0 |
| 2 | Pt—S/C | tetrahydrofuran | 135/15 | 40 |
| 3 | Pt—S/C | 2,5-dimethyltetrahydrofuran | 135/15 | 4 |
| 4 | Pt—S/C | cyclohexane | 135/15 | 7 |
| 5 | Pt—S/C | n-hexanol | 135/15 | 14 |
| 6 | Pt—S/C | 1,2-dichlorobenzene | 135/15 | 15 |

[1]All reactions were run at 250° C. for 8 h.

After establishing that THF is the best solvent for hydrodenitrogenation, the mol % of catalyst relative to starting α-aminocaprolactam that gave the highest yield of caprolactam is determined (Table 6). Optimization of the mol % catalyst is completed prior to optimization of the initial $H_2/H_2S$ atmosphere. Hydrodenitrogenation yields increase as the mol % Pt relative to α-aminocaprolactam was increased from 2 mol % (entry 1, Table 6) to 4 mol % (entry 2, Table 6) to 8 mol % (entry 3, Table 6). However, yields do not increase after the mol % Pt is increased from 8 mol % to 16 mol % (entry 3 vs. entry 4, Table 6).

TABLE 6

Mol % Pt[1]

| Entry | Catalyst | Loading | Solvent | $H_2/H_2S$ (psi/psi) | % Yield |
|---|---|---|---|---|---|
| 1 | Pt—S/C | 2 mol % | THF | 135/15 | 33 |
| 2 | Pt—S/C | 4 mol % | THF | 135/15 | 40 |
| 3 | Pt—S/C | 8 mol % | THF | 135/15 | 44 |
| 4 | Pt—S/C | 16 mol % | THF | 135/15 | 43 |

[1]All reactions were run at 250° C. for 8 h.

Reuse of the Pt catalyst for multiple hydrodenitrogenations of α-aminocaprolactam is also attempted (Table 7). After the initial hydrodenitrogenation, Pt catalyst is recovered. No reactivation or additional presulfiding of the Pt catalyst is employed. The hydrodenitrogenation of α-aminocaprolactam is repeated four times with reused catalyst and results in only a modest reduction in the yield of product caprolactam (Table 7).

TABLE 7

Catalyst Reuse, Pt—S/C

| Entry | Catalyst (8 mol %) | Solvent | Temp (° C.) | $H_2/H_2S$ (psi/psi) | % Yield |
|---|---|---|---|---|---|
| initial run | Pt—S/C | THF | 250 | 90/10 | 58 |
| 1st reuse | Pt—S/C | THF | 250 | 90/10 | 51 |
| 2nd reuse | Pt—S/C | THF | 250 | 90/10 | 50 |
| 3rd reuse | Pt—S/C | THF | 250 | 90/10 | 55 |
| 4th reuse | Pt—S/C | THF | 250 | 90/10 | 47 |

With a reaction temperature, % mol catalyst, time and solvent standardized (250° C., 8 mol %, 8 h, and THF), various catalysts are then tested: Ru on C (Table 8), Rh on C (Table 9), Pd on C (Table 10), Re on C (Table 11), Ir on C (Table 12), and Ni—Mo on C (Table 13). Hydrodenitrogenations in tetrahydrofuran (THF) are catalyzed by the metal on C versus the presulfided metal on C and use of $H_2$ versus $H_2/H_2S$ atmospheres (Table 8-13). For all of the metals examined, running the hydrodenitrogenation with the catalyst under an initial 80 psi/20 psi; $H_2/H_2S$ atmosphere gives higher yields of caprolactam than use of a strictly $H_2$ atmosphere. This trend holds, irrespective of whether the catalyst has been presulfided. The highest hydrodenitrogenation yields (Table 8-13) are achieved when the catalyst is presulfided and run under an initial 80 psi/20 psi; $H_2/H_2S$ atmosphere. Nonetheless, the best yields (Table 8-13) are lower than the 65% yield of caprolactam achieved using presulfided Pt on C under an 80 psi/20 psi; $H_2/H_2S$ atmosphere.

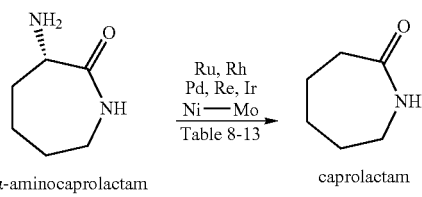

TABLE 8

Ru Hydrodenitrogenation

| Entry | Catalyst (8 mol %) | Temperature (° C.) | $H_2/H_2S$ (psi/psi) | Reaction time (h) | % Yield |
|---|---|---|---|---|---|
| 1 | Ru/C | 250 | 100/0 | 8 | 14 |
| 2 | Ru/C | 250 | 80/20 | 8 | 35 |
| 3 | Ru—S/C | 250 | 100/0 | 8 | 23 |
| 4 | Ru—S/C | 250 | 80/20 | 8 | 42 |

TABLE 9

Rh Hydrodenitrogenation

| Entry | Catalyst (8 mol %) | Temperature (° C.) | $H_2/H_2S$ (psi/psi) | Reaction time (h) | % Yield |
|---|---|---|---|---|---|
| 1 | Rh/C | 250 | 100/0 | 8 | 20 |
| 2 | Rh/C | 250 | 80/20 | 8 | 35 |
| 3 | Rh—S/C | 250 | 100/0 | 8 | 25 |
| 4 | Rh—S/C | 250 | 80/20 | 8 | 39 |

TABLE 10

Pd Hydrodenitrogenation

| Entry | Catalyst (8 mol %) | Temperature (° C.) | $H_2/H_2S$ (psi/psi) | Reaction time (h) | % Yield |
|---|---|---|---|---|---|
| 1 | Pd/C | 250 | 100/0 | 8 | 22 |
| 2 | Pd/C | 250 | 80/20 | 8 | 36 |
| 3 | Pd—S/C | 250 | 100/0 | 8 | 24 |
| 4 | Pd—S/C | 250 | 80/20 | 8 | 37 |

TABLE 11

Re Hydrodenitrogenation

| Entry | Catalyst (8 mol %) | Temperature (° C.) | $H_2/H_2S$ (psi/psi) | Reaction time (h) | % Yield |
|---|---|---|---|---|---|
| 1 | Re/C | 250 | 100/0 | 8 | 10 |
| 2 | Re/C | 250 | 80/20 | 8 | 16 |
| 3 | Re—S/C | 250 | 100/0 | 8 | 18 |
| 4 | Re—S/C | 250 | 80/20 | 8 | 26 |

TABLE 12

Ir Hydrodenitrogenation

| Entry | Catalyst (8 mol %) | Temperature (° C.) | H$_2$/H$_2$S (psi/psi) | Reaction time (h) | % Yield |
|---|---|---|---|---|---|
| 1 | Ir/C | 250 | 100/0 | 8 | 3 |
| 2 | Ir/C | 250 | 80/20 | 8 | 13 |
| 3 | Ir—S/C | 250 | 100/0 | 8 | 18 |
| 4 | Ir—S/C | 250 | 80/20 | 8 | 33 |

TABLE 13

Ni—Mo Hydrodenitrogenation

| Entry | Catalyst (8 mol %) | Temperature (° C.) | H$_2$/H$_2$S (psi/psi) | Reaction time (h) | % Yield |
|---|---|---|---|---|---|
| 1 | Ni—Mo/C | 250 | 100/0 | 8 | 6 |
| 2 | Ni—Mo/C | 250 | 80/20 | 8 | 22 |
| 3 | Ni—Mo—S/C | 250 | 100/0 | 8 | 13 |
| 4 | Ni—Mo—S/C | 250 | 80/20 | 8 | 35 |

Hydrodenitrogenation of α-aminocaprolactam to caprolactam by Au on C are also tested according to the following reaction.

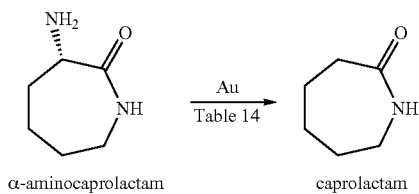

α-aminocaprolactam → caprolactam (Au, Table 14)

This catalyst is found to give the highest yields of caprolactam when the Au was presulfided (Au—S/C) and run under an 80 psi/20 psi; H$_2$/H$_2$S atmosphere (entry 1, Table 14). Given the extensive examination of Au nanoparticle catalysts in the literature, the impact of supports on hydrodenitrogenations of sulfided Au catalysts is tested. See, e.g., M. S. Chen et al., Science 306:252-255 (2004); and A. Corma et al., Science 313:332-334 (2006). Among the supports screened (TiO$_2$, Fe$_2$O$_3$, Co$_2$O$_3$, NiO CuO, MgO), NiO is found to be the best for hydrodenitrogenations using sulfided Au (Au—S/NiO). NiO by itself is capable of catalyzing hydrodenitrogenations albeit in a modest 15% yield (entry 2, Table 14). Without presulfiding, NiO-supported Au does not improve the hydrodenitrogenation yield (entry 3 vs. entry 2, Table 14). Combination of presulfiding (entry 4 vs. entry 3, Table 14), increasing the reaction temperature and decreasing reaction time (entry 5 vs. entry 4, Table 14), and changing the initial H$_2$/H$_2$S atmosphere (entry 6 vs. entry 5, Table 14) improves hydrodenitrogenation yields. The highest yield (62%) using sulfided, NiO-supported Au (entry 6, Table 14) is approximately the same as the yield (65%) that for sulfided Pt on C.

TABLE 14

NiO-Supported Au Hydrodenitrogenation

| Entry | Catalyst (8 mol %) | Temperature (° C.) | H$_2$/H$_2$S (psi/psi) | Reaction time (h) | % Yield |
|---|---|---|---|---|---|
| 1 | Au—S/C | 250 | 80/20 | 8 | 40 |
| 2 | NiO | 250 | 80/20 | 8 | 15 |
| 3 | Au/NiO | 250 | 80/20 | 8 | 14 |

TABLE 14-continued

NiO-Supported Au Hydrodenitrogenation

| Entry | Catalyst (8 mol %) | Temperature (° C.) | H$_2$/H$_2$S (psi/psi) | Reaction time (h) | % Yield |
|---|---|---|---|---|---|
| 4 | Au—S/NiO | 250 | 80/20 | 8 | 20 |
| 5 | Au—S/NiO | 300 | 80/20 | 4 | 54 |
| 6 | Au—S/NiO | 300 | 45/5 | 4 | 62 |

Example 3

Hydrodenitrogenation of L-Lysine to Caprolactam

Direct conversion of L-lysine into caprolactam is attempted (Table 15). This is tested using presulfided Pt on C (1 mol %) in dried EtOH under an initial 90 psi/10 psi; H$_2$/H$_2$S. After heating at 250° C. for 8 h, L-lysine is found to be converted into caprolactam in 15% yield.

TABLE 15

Direct Conversion of L-Lysine into Caprolactam

L-lysine → caprolactam (Pt-S/C, Table 15)

| Catalyst (1 mol %) | Solvent | Temp (° C.) | H$_2$/H$_2$S (psi/psi) | Reaction time (h) | % Yield |
|---|---|---|---|---|---|
| Pt-S/C | EtOH | 250 | 90:10 | 8 | 15 |

The examples and other embodiments described herein are exemplary and not intended to be limiting in describing the full scope of compositions and methods of this technology. Equivalent changes, modifications and variations of specific embodiments, materials, compositions and methods may be made within the scope of the present technology, with substantially similar results.

What is claimed is:

1. A process for preparing caprolactam, the process comprising contacting lysine, alpha aminocaprolactam or a salt thereof, with a transition metal catalyst and hydrogen gas or a hydrogen gas mixture, optionally in the presence of a solvent.

2. The process according to claim 1, wherein said transition metal catalyst comprises Pt, Au, Pd, Rh, Re, Ru, Ir, Ni, or Mo.

3. The process according to claim 1, wherein said transition metal catalyst comprises a sulfided transition metal catalyst.

4. The process according to claim 3, wherein said sulfided transition metal catalyst comprises sulfided Pt, Au, Pd, Rh, Re, Ru, Ir, Ni, or Mo.

5. The process according to claim 1, wherein said transition metal catalyst is provided on a support material.

6. The process according to claim 5, wherein said support material comprises carbon, SiO$_2$, Al$_2$O$_3$, TiO$_2$, ZrO$_2$, aluminosilicates, silica-titania, titania-alumina, or NiO.

7. The process according to claim 1, wherein said contacting is conducted in the presence of a solvent, and said solvent comprises tetrahydrofuran or ethanol.

8. The process according to claim 1, wherein said hydrogen gas or hydrogen gas mixture is a hydrogen gas mixture comprising $H_2S$.

9. The process according to claim 8, wherein said hydrogen gas mixture comprises from about 5 to about 50 vol-% of said $H_2S$.

10. The process according to claim 1, wherein said contacting with said hydrogen gas or hydrogen gas mixture is at a pressure from about 50 to about 3000 psi at the start of said process.

11. The process according to claim 1, wherein contacting is conducted at a temperature of from about 50° C. to about 300° C.

12. The process according to claim 11, wherein said temperature is from about 250° C. to about 300° C.

13. The process according to claim 1, wherein said contacting is performed for about 0.1 to about 8 hours.

14. The process according to claim 1, wherein said lysine is L-lysine.

15. The process according to claim 7, wherein said solvent comprises ethanol.

16. The process according to claim 1, wherein said process further comprises isolating said caprolactam produced thereby.

17. The process according to claim 1, wherein said process is conducted in a single step.

18. A process for preparing pipecolinic acid, comprising the step of contacting lysine with a transition metal catalyst, and hydrogen gas or a hydrogen gas mixture, in the presence of a solvent comprising water.

19. The process according to claim 18, wherein said transition metal catalyst comprises Pt, Au, Pd, Rh, Re, Ru, Ir, Ni or Mo.

20. The process according to claim 19, wherein said transition metal catalyst comprises a Pd, Ru, or Raney Ni catalyst.

21. The process according to claim 18, wherein said transition metal catalyst is provided on a support material comprising carbon, $SiO_2$, $Al_2O_3$, $TiO_2$, $ZrO_2$, aluminosilicates, silica-titania, or titania-alumina.

22. The process according to claim 18, wherein said hydrogen gas mixture comprises $H_2S$.

23. The process according to claim 18, wherein said contacting with said hydrogen gas or hydrogen gas mixture is at a pressure from about 100 to about 3000 psi at the start of said process.

24. The process according to claim 18, wherein contacting is conducted at a temperature of from about 50° C. to about 300° C.

25. The process according to claim 24, wherein said temperature is about 200° C.

26. The process according to claim 18, wherein said contacting is performed for about 0.1 to about 8 hours.

27. The process according to claim 18, wherein said lysine is L-lysine.

28. The process according to claim 18 wherein said process further comprises isolating said pipecolinic acid produced thereby.

29. A process for preparing caprolactam, the process comprising: (a) heating lysine or salt thereof to a temperature of about 50° C. to 300° C., optionally in the presence of a first transition metal catalyst to produce a first reaction product comprising alpha amino caprolactam: (b) contacting said first reaction product with hydrogen gas or a hydrogen gas mixture and a second transition metal catalyst to produce a second reaction product comprising caprolactam; (c) recovering caprolactam from the second reaction product to produce a recovered caprolactam.

30. A process according to claim 29, wherein said heating is conducted in the presence of said first transition metal catalyst.

31. A process according to claim 30, wherein said first transition metal catalyst is the same as said second transition metal catalyst.

32. The process according to claim 31 wherein said transition metal catalyst comprises Pt, Au, Pd, Rh, Re, Ru, Ir, Ni, or Mo.

33. The process according to claim 31, wherein said transition metal catalyst comprises a sulfided transition metal catalyst.

34. The process according to claim 33, wherein said sulfided transition metal catalyst comprises sulfided Pt, Au, Pd, Rh, Re, Ru, Ir, Ni, or Mo.

35. The process according to claim 29, wherein said transition metal catalyst is provided on a support material.

36. The process according to claim 35, wherein said support material comprises carbon, $SiO_2$, $Al_2O_3$, $TiO_2$, $ZrO_2$, aluminosilicates, silica-titania, titania-alumina, or NiO.

37. A process according to claim 29, wherein heating is conducted in the presence of a solvent.

38. The process according to claim 37, wherein said solvent comprises tetrahydrofuran or ethanol.

39. The process according to claim 29, wherein said hydrogen gas or hydrogren gas mixture is a hydrogen gas mixture comprising $H_2S$.

40. The process according to claim 39, wherein said hydrogen gas mixture comprises about 5 to about 50 vol-% of said $H_2S$.

41. The process according to claim 29, wherein said contacting with said gas is at a pressure from about 50 to about 3000 psi at the start of said contacting step.

42. The process according to claim 29, wherein said contacting is conducted at a temperature of from about 50° C. to about 300° C.

43. The process according to claim 42, wherein said temperature is from about 250° C. to about 300° C.

44. The process according to claim 29, wherein said reaction is performed for about 0.1 to about 8 hours.

45. The process according to claim 29, wherein the alpha aminocaprolactam is alpha-L-aminocaprolactam.

46. The process according to claim 29, wherein said process further comprises isolating caprolactam produced thereby.

* * * * *

UNITED STATES PATENT AND TRADEMARK OFFICE
CERTIFICATE OF CORRECTION

PATENT NO. : 8,283,466 B2  Page 1 of 1
APPLICATION NO. : 12/527848
DATED : October 9, 2012
INVENTOR(S) : John W. Frost It is certified that error appears in the above-identified patent and that said Letters Patent is hereby corrected as shown below:

Title Page 2, item (56), Other Publications, Frow, E.K. et al,
 "Meddicinal" should be -- Medicinal --

Title Page 3, item (56), Other Publications, Zhang et al,
 "porpylene" should be -- propylene --

In the Specification:

Col. 1, line 37, "used" should be -- use --

Col. 12, line 49, delete "to"

Col. 13, line 2, delete first occurrence of "to"

In the Claims:

Col. 20, line 5, claim 29, "caprolactam:" should be -- caprolactam; --

Signed and Sealed this
Seventeenth Day of September, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,283,466 B2 | Page 1 of 1 |
| APPLICATION NO. | : 12/527848 | |
| DATED | : October 9, 2012 | |
| INVENTOR(S) | : John W. Frost | |

It is certified that error appears in the above-identified patent and that said Letters Patent is hereby corrected as shown below:

In the Specification:
Column 1, Line 11 delete "STATEMENT OF GOVERNMENT INTEREST The present work was performed in part with funding from the U.S. National Science Foundation, Grant No. NSF CHE0211375. The U.S. Government may have certain rights in this technology." and insert therefor:

--GOVERNMENT LICENSE RIGHTS

This invention was made with government support under CHE0211375 awarded by the National Science Foundation. The government has certain rights in the invention.--

Signed and Sealed this
Thirteenth Day of May, 2014

Michelle K. Lee
*Deputy Director of the United States Patent and Trademark Office*